(12) United States Patent
Leight

(10) Patent No.: US 9,763,832 B2
(45) Date of Patent: Sep. 19, 2017

(54) PULL OUT EARPLUG

(71) Applicant: Howard S. Leight, Santa Monica, CA (US)

(72) Inventor: Howard S. Leight, Santa Monica, CA (US)

( * ) Notice: Subject to any disclaimer, the term of this patent is extended or adjusted under 35 U.S.C. 154(b) by 0 days.

(21) Appl. No.: 13/860,388

(22) Filed: Apr. 10, 2013

(65) Prior Publication Data

US 2014/0305733 A1    Oct. 16, 2014

(51) Int. Cl.
*A61F 11/08*    (2006.01)

(52) U.S. Cl.
CPC ......... *A61F 11/08* (2013.01); *Y10T 29/49826* (2015.01)

(58) Field of Classification Search
CPC ........ A61F 11/00; A61F 11/008; A61F 11/04; A61F 11/06; A61F 11/08; A61F 11/10; H04R 1/1016; H04R 1/10; H04R 1/1091; H04R 1/1058; H04R 1/1033
USPC .......................... 381/380, 325, 329; 128/864
See application file for complete search history.

(56) References Cited

U.S. PATENT DOCUMENTS

| | | | | |
|---|---|---|---|---|
| 2,094,534 A * | 9/1937 | Halle | ....................... | A61F 11/08 128/864 |
| 2,785,675 A * | 3/1957 | Berkman | ................. | A61F 11/08 128/867 |
| 3,943,925 A | 3/1976 | Leight | | |
| 3,970,082 A | 7/1976 | Leight | | |
| 4,089,332 A * | 5/1978 | Rose | ....................... | A61F 11/08 128/865 |
| D253,723 S | 12/1979 | Leight | | |
| 4,193,396 A * | 3/1980 | Wacker | .................... | A61F 11/08 128/864 |
| 4,253,452 A * | 3/1981 | Powers | .................... | A61F 11/08 128/864 |
| 4,434,794 A | 3/1984 | Leight | | |
| 4,490,857 A | 1/1985 | Leight | | |
| 4,579,112 A * | 4/1986 | Scott | ....................... | A61F 11/08 128/864 |
| 4,750,669 A | 6/1988 | Leight | | |
| 4,774,938 A | 10/1988 | Leight | | |
| 4,819,624 A | 4/1989 | Leight | | |
| 4,916,758 A * | 4/1990 | Jordan-Ross | .......... | A45D 44/12 128/866 |
| 5,003,608 A * | 3/1991 | Carlson | .................... | A61B 5/12 381/322 |
| 5,074,375 A * | 12/1991 | Grozil | ..................... | A61F 9/029 128/864 |
| D329,897 S | 9/1992 | Leight | | |
| 5,203,352 A * | 4/1993 | Gardner, Jr. | ............ | A61F 11/10 128/864 |
| D335,342 S | 5/1993 | Leight | | |
| D340,282 S | 10/1993 | Leight | | |
| D341,656 S | 11/1993 | Leight | | |
| 5,280,845 A | 1/1994 | Leight | | |
| 5,285,925 A | 2/1994 | Leight | | |

(Continued)

*Primary Examiner* — Davetta W Goins
*Assistant Examiner* — Jasmine Pritchard
(74) *Attorney, Agent, or Firm* — Lawrence S. Cohen

(57) ABSTRACT

An earplug for blocking sound can be installed uniformly deep in a person's ear canal and can be easily withdrawn. The earplug includes a foam cylinder (12) and a string (14) extending in a loop from the rear of the cylinder, with opposite front ends (32, 34) of the string loop projecting into the body and held therein as by adhesive (38).

12 Claims, 1 Drawing Sheet

(56) References Cited

U.S. PATENT DOCUMENTS

| | | | |
|---|---|---|---|
| 5,298,691 A | 3/1994 | Leight | |
| 5,322,185 A | 6/1994 | Leight | |
| 5,372,278 A | 12/1994 | Leight | |
| D371,840 S | 7/1996 | Leight | |
| D372,776 S | 8/1996 | Leight | |
| 5,711,313 A * | 1/1998 | Fleming | A61F 11/12 128/864 |
| 5,724,119 A | 3/1998 | Leight | |
| 5,727,566 A | 3/1998 | Leight | |
| D395,657 S | 6/1998 | Leight | |
| 5,811,742 A | 9/1998 | Leight | |
| D400,248 S | 10/1998 | Leight | |
| 5,824,966 A | 10/1998 | Leight | |
| D405,521 S | 2/1999 | Leight | |
| D413,379 S | 8/1999 | Leight | |
| 5,979,451 A | 11/1999 | Leight | |
| 5,996,123 A | 12/1999 | Leight | |
| 5,996,584 A * | 12/1999 | Oliveira | A61F 11/08 128/864 |
| 6,006,857 A | 12/1999 | Leight | |
| D426,880 S | 6/2000 | Leight | |
| D427,382 S | 6/2000 | Leight | |
| 6,105,715 A * | 8/2000 | Knauer | A61F 11/08 128/864 |
| 6,138,790 A | 10/2000 | Leight | |
| 6,148,446 A | 11/2000 | Leight | |
| D442,340 S | 5/2001 | Leight | |
| 6,241,041 B1 | 6/2001 | Leight | |
| 6,298,493 B1 * | 10/2001 | Ambroise | A45D 44/12 128/866 |
| 6,299,019 B1 | 10/2001 | Leight | |
| 6,345,684 B1 * | 2/2002 | Leight | A61F 11/10 128/864 |
| 6,695,093 B1 * | 2/2004 | Falco | A61F 11/08 181/130 |
| 7,185,655 B1 * | 3/2007 | Redon | A61F 11/08 128/864 |
| 7,250,021 B2 | 7/2007 | Leight | |
| D560,792 S * | 1/2008 | Miller | A61F 11/08 D24/106 |
| 7,457,428 B2 * | 11/2008 | Vaudrey | A61F 11/12 381/372 |
| 7,984,716 B2 * | 7/2011 | Purcell | A61F 11/08 128/865 |
| 8,498,440 B2 * | 7/2013 | Parkins | H04R 1/1016 381/328 |
| 8,556,024 B2 * | 10/2013 | Hakansson | A61F 11/08 181/130 |
| 8,616,214 B2 * | 12/2013 | Park | A61F 11/10 128/864 |
| 8,671,948 B2 * | 3/2014 | Turdjian | A61F 11/08 128/864 |
| 8,708,091 B2 * | 4/2014 | Barwacz | A61F 11/08 181/135 |
| 2005/0150715 A1 * | 7/2005 | Barnes | A61F 11/12 181/135 |
| 2006/0045297 A1 * | 3/2006 | Haussmann | A61F 11/08 381/322 |
| 2008/0144871 A1 * | 6/2008 | Purcell | A61F 11/10 381/329 |
| 2010/0121285 A1 * | 5/2010 | Illi | A61F 11/00 604/286 |
| 2012/0272974 A1 * | 11/2012 | Magidson | A61F 11/12 128/864 |
| 2014/0215696 A1 * | 8/2014 | Polit | A61F 11/08 2/423 |

* cited by examiner

PULL OUT EARPLUG

BACKGROUND OF THE INVENTION

One type of earplug designed for low cost production, consists of an elongated foam body with a tapered front end for insertion into the ear canal, and with a flared rear end that projects slightly from the rear of the ear canal. The earplug body often is formed of a slow recovery foam that can be compressed to a small diameter for deep insertion before returning to its original diameter. After use, the projecting rear end can be grasped between the thumb and index fingers to pull the earplug out of the ear canal. People who have not used such an earplug many times before, are often concerned that they will not be able to remove the earplug and are reluctant to insert the earplug deeply enough and hold it in position for about a half minute while it expands, to assure good sound blocking.

SUMMARY OF THE INVENTION

In accordance with one embodiment of the invention, a low cost noise blocking earplug is provided that assures the wearer that the earplug can be easily removed. The earplug includes a foam earplug body and a flexible string that has opposite ends projecting into the body rear portion and fixed in place thereat, and that forms a loop behind the body. The foam body is short in length, and is forwardly inserted deeply enough that the rear end of the body lies approximately flush with the rear end of the ear canal. The string loop can be pulled to pull the rear portion of the body rearward, which prevents the earplug body from tipping and jamming in place.

The novel features of the invention are set forth with particularity in the appended claims. The invention will be best understood from the following description when read in conjunction with the accompanying drawings.

DESCRIPTION OF THE PREFERRED EMBODIMENTS

Figure 1:
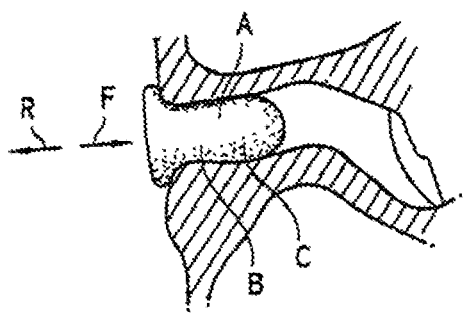
FIG. 1 is a side elevation view of a prior art earplug, after it has been inserted into the ear canal of a wearer.

FIG. 1 shows a prior art earplug A of the type described in U.S. Pat. No. 4,774,938, which is molded of slow recovery foam, and which is elongated, with a diameter at an axially middle portion of about 11 millimeters, and with a length of about 25 millimeters. A person rolls the axial middle B and front C of the earplug in his/her fingers to reduce its diameter, and then inserts the earplug into his ear canal. The earplug is supposed to be held deeply inserted while the foam recovers towards its original diameter, to provide a firm sealing fit within the ear canal as is shown in FIG. 1. However, workers are reluctant to hold a deeply inserted earplug and as a result there is often a poor sealing against sound. A supervisor who looks at the worker=s ear finds it difficult to determine whether or not the earplug has been deeply installed.

Figure 2:
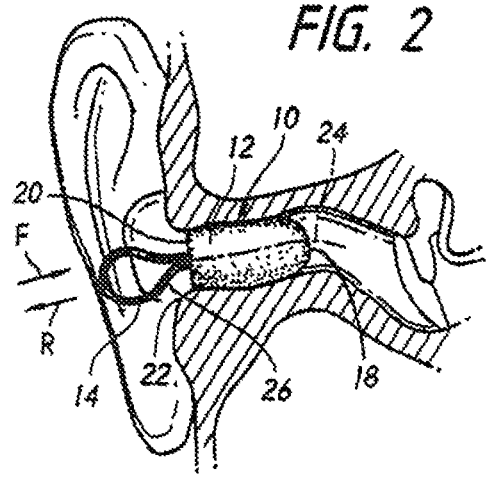
FIG. 2 is a side elevation view of an earplug of one embodiment of the invention after it has been inserted into a wearer=s ear canal.
Figure 3:
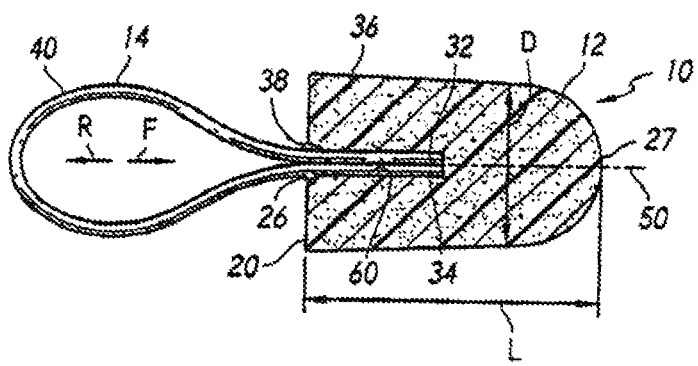
FIG. 3 is a sectional side view of the earplug of FIG. 2.

FIGS. 2 and 3 show an earplug 10 of a first embodiment of the invention, which includes a foam body 12 having a front end 18 and a rear end 20 and a pull out handle in the form of a flexible string 14. The foam body is of cylindrical shape along a majority of its length (preferably at least 70% of its length), with a diameter D of 12 millimeters (11 to 14 mm) and a length L of 20 millimeters (18 to 23 mm). These dimensions allow the earplug to be inserted into the ear canal of a majority of people with the front end 18 inserted and the body 12 moved in until the rear end 20 of the earplug body lies approximately flush (within 3 millimeters) with the ear canal entrance. The entrance 22 is where the ear canal walls are angled 45° from the canal axis 24. A person presses his index finger inward (forward F) along the ear canal axis until his finger simultaneously touches the entrance 22 and lies against the middle 26 of the rear end 20 of the foam cylindrical body. The foam body can be constructed of slow recovery foam or of instant recovery foam (or anything in between). By describing the earplug body as substantially cylindrical, applicant means that the expansion angle is no more than 12E.

FIG. 3 shows that the flexible string 14 has opposite ends 32, 34 that are fixed to the earplug body at locations that lie at the rear portion 36 of the body. Applicant uses a quantity 38 of adhesive to fix the string ends in place. The string opposite ends are connected by a loop 40 of the string. To remove the earplug from his ear canal, a person pulls on the loop 40. There is no need for the rear end 20 of the body to project rearward R beyond the entrance of the ear canal. A person who intends to insert the earplug body into his ear canal, can see that the ear plug body is short and can see that the string allows pull out of the earplug, all of which gives him/her confidence that the ear plug can be removed even if it is deeply installed.

Figure 5:
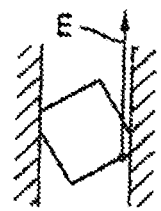
FIG. 5 shows a jammed earplug of the prior art.

It would be possible to install the ends 32, 34 of the string so they (their rearmost ends) are fixed to the axial front portion 27 of the earplug body, that is, to a location that lies closer to the body front end 27 than to the body rear end 20. However, this can lead to jamming during earplug pullout, where the short earplug tips so the earplug body axis 50 is considerably angled (e.g. more than) 7° from the ear canal axis 24. Such jamming is shown in FIG. 5 as a result of a pullout force E. Applicant's fixing of the string ends to the rear portion (36) of the earplug avoids such jamming.

Applicant prefers to mold the earplug body with a short passage 60, where the string ends will fit. When the string ends are installed in the passage, the flowable adhesive 38 is injected and allowed to solidify. Instead of using a string with a loop, it would be possible to insert only a length of string. However, a loop is easier to pull out than a single length of string that can slip on the fingers. Also, if one end of the loop becomes loose, there is still the other end of the loop in position to be pulled out. Applicant uses a string of flexible plastic having a diameter of 1.4 millimeters.

When a worker places an earplug in his ear canal, a supervisor can determine that the earplug was installed by noting that he can see the loop of string and can hardly see the earplug body. For this reason, the string is preferably made of a material having a bright color (i.e., not flesh colored) different from the body color. If he wishes, the supervisor can look closely to see that the rear end of the earplug body lies at the entrance to the ear canal, rather than projecting rearward R out of the ear canal. By encouraging uniform installation, applicant's earplug encourages proper installation to protect workers' hearing.

Figure 4:
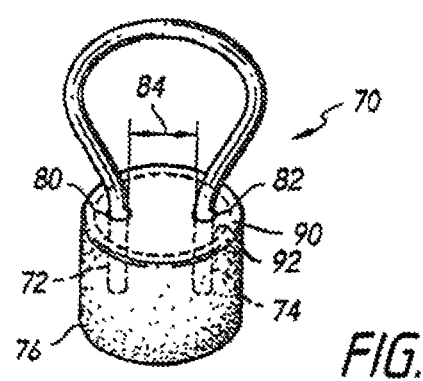
FIG. 4 is a rear and side isometric view of a modified earplug of the invention.

FIG. 4 shows a modified earplug 70 that has a loop with opposite ends 72, 74 that are joined to the earplug body 76 at locations 80, 82 that are spaced a distance 84 apart, where the distance is more than the diameter of the string. The locations lie within an inner part 92 of the earplug body that lies further from the body periphery than the string diameter (1.4 mm). The locations 80, 82 lie in the inner part 92 of the body (that lies within the outer portion 90). The string ends are separately adhered by adhesive to the body, which increases the likelihood that at least one string end will always remain in the body.

Applicant prefers that the earplug body have a length L of 20 millimeters (18 to 20 mm). Also, applicant prefers that the rear end 20 of the body lie between 3 millimeters, and preferably 2 millimeters, forward F of the entrance 22 to the ear canal, and no more than 3 millimeters rearward R of the entrance. Applicant finds that a more forward location can result in the earplug hurting the wearer, while a more rearward location results in reduced sound attenuation.

Thus, the invention provides an earplug that encourages proper installation by assuring the wearer that the earplug body is small and later can be pulled out by pulling on the loop of a string. The string has opposite ends that are attached to a rear portion of the foam ear plug body. This can be done by inserting the string ends into a single hole in the rear of the body, or into separate holes that lie in a middle portion of the body, and using adhesive to hold the ends in place.

Although particular embodiments of the invention have been described and illustrated herein, it is recognized that modifications and variations may readily occur to those skilled in the art, and consequently, it is intended that the claims be interpreted to cover such modifications and equivalents.

What is claimed is:

1. An earplug for blocking sound to a person, comprising:
   a foam body that is completely insertable into a person's ear canal, said body having a front portion and a rear portion and a rear end (20); and,
   a string of flexible plastic that has opposite string ends that both project into said foam body rear end and into said foam body rear portion and that are each fixed to the foam body at locations that lie at the foam body rear portion, said string extending between said opposite string ends in the form of a self standing open loop said loop extending behind said foam body.

2. The earplug described in claim 1 wherein:
   said foam body is of substantially cylindrical shape along a majority of its length and fits completely into the person's ear canal so that said rear end of said body lies no further forward (F) than the entrance (22) to the person's ear canal.

3. An earplug for blocking noise from passing through the ear canal of a person, comprising:
   a foam body having a length and a diameter to fit into a person's ear canal and block sound, and a string of flexible plastic having a string diameter;
   said body having a substantially cylindrical periphery along a majority of its length and having an outer portion (90) and an inner part (92) lying radially within said outer portion, said inner part lying further from said body periphery than said string diameter; and,
   said string extending in the form of a self standing open loop for pulling said body from the ear canal, and with opposite ends of said loop each projecting forward into a rear end of said body in said inner part and fixed to said body at locations (80, 82) spaced apart a distance (84) greater than said string diameter and fixed to the body within a rear portion of the body, and with said loop extending rearward of said body.

4. The earplug described in claim 3 wherein:
   said foam body has a substantially cylindrical shape with an average diameter of 11 to 14 millimeters and an axial length of 20 millimeters.

5. The earplug described in claim 3 wherein:
   said loop opposite ends have locations (80, 82) where they enter said body spaced apart (84) by a distance more than two of said string diameter.

6. A method for constructing and installing an earplug in a person's ear to block sound to be fitted so that an earplug body rear end is approximately flush with the ear canal entrance, comprising:
   constructing the earplug so it consists of a foam body of substantially cylindrical shape along a majority of its length, with a body rear end, a body rear portion and a plastic string formed into a self standing open loop that has opposite strings ends that both project into said body rear end and are fixed in place in the body rear portion;
   inserting a front end (18) of said body into the person's ear canal as follows;
   a person taking hold of the loop of the earplug between two fingers such that one or both of the tips of the fingers is in contact with the body rear end;
   guiding the body into the ear canal by pushing on the loop as held between two fingers and also pressing on the body rear end (20) with the tip of at least one finger until at least one of the finger tips simultaneously touches the ear canal entrance (22) and lies against the rear end of the body and the body lies substantially completely within the ear canal, and the loop can be seen from outside the ear.

7. The method described in claim 6 wherein:
   said earplug body rear end lays no further rearward than the entrance to the person's ear canal.

8. The method of claim 6 wherein the body is formed of a slow recovery foam and the body is rolled between the user's fingers to reduce its diameter and it is then inserted into the ear canal.

9. The method of claim 8 wherein the at least one finger remains in contact with the body to keep it in place while the foam recovers to be in contact with the ear canal.

10. The method of claim 6 further comprising removing the earplug from the person's ear canal by pulling on the loop.

11. An earplug for blocking sound to a person, and presenting a loop that can be observed when the earplug has been inserted and can be used to remove the earplug from its installation in a user's ear comprising:
    a foam body that is completely insertable into a person's ear canal; and,
    a string of flexible plastic that has opposite string ends that both project into said foam body rear end and into and terminating within said foam body and that are fixed to the foam body, said string extending in the form of a self standing open loop said loop extending behind said foam body whereby the foam body may be fully inserted by a user's finger while the earplug is guided into place by holding the loop with the finger in contact with the foam plug.

12. The earplug of claim 11 wherein:
the body is formed of a slow recovery foam and the body is rolled between the user's fingers to reduce its diameter and it is then inserted into the ear canal whereupon it recovers into contact with the ear canal while the user's finger places it in the ear canal.

\* \* \* \* \*